(12) United States Patent
Wang et al.

(10) Patent No.: US 11,903,932 B2
(45) Date of Patent: Feb. 20, 2024

(54) USE OF DIHYDROBERBERINE OR ITS DERIVATIVES TO ENHANCE MUSCLE FUNCTION

(71) Applicant: NANJING NUTRABUILDING BIO-TECH CO., LTD., Nanjing (CN)

(72) Inventors: Mingru Wang, Nanjing (CN); Ronghua Yi, Nanjing (CN); Shawn Wells, Lewisville, TX (US); Kylin Liao, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 0 days.

(21) Appl. No.: 17/976,066

(22) Filed: Oct. 28, 2022

(65) Prior Publication Data
US 2023/0138576 A1 May 4, 2023

(30) Foreign Application Priority Data

Nov. 2, 2021 (WO) ................ PCT/CN2021/128231

(51) Int. Cl.
*A61K 31/4375* (2006.01)
*A61P 21/00* (2006.01)
(52) U.S. Cl.
CPC .......... *A61K 31/4375* (2013.01); *A61P 21/00* (2018.01)

(58) Field of Classification Search
None
See application file for complete search history.

(56) References Cited

U.S. PATENT DOCUMENTS

2006/0223838 A1* 10/2006 Jiang ................. A61K 31/4375
514/284
2010/0113494 A1* 5/2010 Hu ............................ A61P 3/06
514/279

OTHER PUBLICATIONS

Dihydroberberine 150 mg, sold by Endurance product company.*

* cited by examiner

*Primary Examiner* — Rei Tsang Shiao
(74) *Attorney, Agent, or Firm* — ANOVA LAW GROUP, PLLC (57) ABSTRACT

The present invention provides novel methods for enhancing muscle function in a mammal, the method includes administration to the mammal of a composition comprising therapeutically effective amount of dihydroberberine (DHB) or a pharmaceutically acceptable salt, acid, ester, analog or derivative thereof. The present invention also provides a composition including therapeutically effective amount of dihydroberberine (DHB) or a pharmaceutically acceptable salt, acid, ester, analog or derivative thereof, for enhancing muscle function. In addition, the present invention provides methods for preparing any compositions disclosed herein.

10 Claims, 6 Drawing Sheets

USE OF DIHYDROBERBERINE OR ITS DERIVATIVES TO ENHANCE MUSCLE FUNCTION

CROSS REFERENCE TO RELATED APPLICATION

This application claims the benefit of a PCT International Application Number PCT/CN2021/128231, filed on Nov. 2, 2021, the content of which is hereby incorporated by reference in its entirety for all purposes.

TECHNICAL FIELD

The present invention generally relates to compositions, methods of preparing such compositions, and method of using such compositions for enhancing muscle function in a mammal.

BACKGROUND

There are three types of muscles in mammals: skeletal muscle, smooth muscle, and cardiac muscle. Skeletal muscle is the most significant part of muscle: it accounts for approximately 40% of total body mass, is attached to the bones, and is involved in the functioning of different parts of the body. For example, it allows us to locomote, such as running, walking, talking, and moving the eyes, head, limbs, or digits when it contracts. Skeletal muscle also controls all facial expressions, including smiles, frowns, breath, and mouth and tongue movements. Moreover, skeletal muscle also generates heat when it contracts and releases, and this helps maintain body temperature. Nearly 85% of the heat that the body produces comes from muscle contraction. Additionally, skeletal muscle also represents an important nutrient store and metabolic regulator. Last but not least, skeletal muscle is a mitochondrion-rich tissue, accounting for approximately 80% of postprandial blood glucose uptake in normal state. Therefore, skeletal muscle is fundamentally important for human life and health.

Unfortunately, since many modern people have unhealthy lifestyles and diets, the decline of skeletal muscle metabolism and function, known as muscular dysfunction, is common and inevitable. Once the muscular dysfunction occurs, it will have severe health consequences, such as impaired locomotory function, compromised balance, inadequate carbohydrate metabolism (like obesity and diabetes), increased risk of fall and fractures, all of which diminish the quality of life in the daily life. Based on some relevant theories, muscular dysfunction is closely linked to the oxidative capacity of skeletal muscle, which is predominately dependent on mitochondria. As such, there is growing evidence suggesting that mitochondrial dysfunction and the associated impairment of fatty acid oxidation, may directly cause muscular strength and insulin resistance (Civitarese, A. E., et al., *Role of adiponectin in human skeletal muscle bioenergetics*. Cell Metabolism, 2006. 4(1): p. 75-87).

Thus, it is important and urgent to develop products or methods that could enhance or improve mitochondrial biogenesis in skeletal muscle to facilitate the improvement of muscular strength and reduce insulin resistance.

SUMMARY OF THE PRESENT INVENTION

In a first aspect, the present invention provides methods for enhancing muscle function in a mammal, the method includes administration to the mammal of a composition including an effective amount of dihydroberberine (DHB) or a pharmaceutically acceptable salt, acid, ester, analog or derivative thereof.

In some embodiments, the enhancing muscle function includes: alleviating or inhibiting muscular dysfunction, improving mitochondrial function in muscle, ameliorating insulin resistance in muscle, increasing muscle mass or muscular strength, mitigating or preventing muscle loss, or boosting exercise performance.

In some embodiments, the enhancing muscle function is increasing muscle mass.

In some embodiments, the enhancing muscle function is improving insulin resistance in skeletal muscle.

In some embodiments, the enhancing muscle function is changing morphology of skeletal muscle, such as increasing number of skeletal muscle fibers and making adjacent muscle fibers align tightly.

In some embodiments, the enhancing muscle function is by increasing ATP production, scavenging chronic ROS, or activating AMPK/SIRT1/PGC-1α mitochondrial biogenesis signaling pathway in muscle tissue.

In some embodiments, the mammal is a human, a cattle, or a pet.

In some embodiments, the composition is prepared in a form of food, drink, nutritional supplement, cosmetic product, or pharmaceutical composition.

In some embodiments, DHB or its analog or its derivatives are administered at a daily dose of 10 mg-2000 mg. Preferably, it is administered at daily doses of 1 mg to 1000 mg, 5 mg to 800 mg, and 10 mg to 500 mg.

In some embodiments, the daily dose is administered in divided doses or a single dose.

In some embodiments, the administration is at least once a day or more times a day.

In some embodiments, the administration is at least 7 days and above in one period.

In some embodiments, the administration is through various routes selected from oral, intravenous injectable, intramuscular injectable, intraperitoneal, topical, or sublingual route.

In some embodiments, dihydroberberine (DHB) or its analog or its derivatives are salts, polymers, esters, or acid.

In some embodiments, dihydroberberine (DHB) or its analog or its derivatives are formulated in solutions, liquid suspensions, parenteral solutions, injections, microemulsion, tablets, pills, granules, powders, film, (micro)capsules, aerosols, tonics, or syrups, beverages, nutritional supplements, snacks, gums, bars, sugars, sublingual articles, or functionalized foods.

In a second aspect, the present invention provides a composition including an effective amount of dihydroberberine (DHB) or a pharmaceutically acceptable salt, acid, ester, analog or derivative thereof, for enhancing muscle function in a mammal.

In some embodiments, the enhancing muscle function includes: alleviating or inhibiting muscular dysfunction, improving mitochondrial function in muscle, ameliorating insulin resistance in muscle, increasing muscle mass or muscular strength, mitigating or preventing muscle loss, boosting exercise performance.

In some embodiments, the enhancing muscle function is improving insulin resistance in skeletal muscle, or changing morphology of skeletal muscle, such as increasing number of skeletal muscle fibers, and making adjacent muscle fibers align tightly.

In some embodiments, the enhancing muscle function is by increasing ATP production, scavenging chronic ROS, or activating the AMPK/SIRT1/PGC-1α mitochondrial biogenesis signaling pathway.

In some embodiments, the mammal is a human, a cattle, or a pet.

In some embodiments, the composition is prepared in a form of food, drink, nutritional supplement, cosmetic product, or pharmaceutical composition.

In some embodiments, dihydroberberine (DHB) or its analog or its derivatives are salts, polymers, esters, or acid.

In some embodiments, the composition is formulated in solutions, liquid suspensions, parenteral solutions, injections, microemulsion, tablets, pills, granules, powders, film, (micro)capsules, aerosols, tonics, or syrups, beverages, nutritional supplements, snacks, bars, sugars, sublingual articles, or functionalized foods.

In some embodiments, the composition is administrated at a daily dose of 10 mg-2000 mg. Preferably, it is administered at daily doses of 1 mg to 1000 mg, 5 mg to 800 mg, and 10 mg to 500 mg.

In a third aspect, the present invention provides use of an effective amount of dihydroberberine or a pharmaceutically acceptable salt, acid, ester, analog or derivative in manufacturing a composition, for enhancing muscle function in a mammal.

In some embodiments, DHB or its analog or its derivatives are administrated at a daily dose of 10 mg-2000 mg. Preferably, it is administered at daily doses of 1 mg to 1000 mg, 5 mg to 800 mg, and 10 mg to 500 mg.

In some embodiments, the enhancing muscle function is increasing muscle mass, improving insulin resistance in skeletal muscle, or changing morphology of skeletal muscle, such as increasing number of skeletal muscle fibers, and making adjacent muscle fibers align tightly.

In some embodiments, the enhancing muscle function is by increasing ATP production, scavenging chronic ROS, or activating the AMPK/SIRT1/PGC-1α mitochondrial biogenesis signaling pathway.

In some embodiments, the daily dose is administered in divided doses or a single dose.

In some embodiments, the administration is at least once a day or more times a day.

In some embodiments, the administration is at least 7 days and above in one period.

In some embodiments, where the administration is through various routes selected from oral, intravenous injectable, intramuscular injectable, intraperitoneal, topical, or sublingual route.

In a fourth aspect, the present invention provides a method for preparing any composition described herein.

In a fourth aspect, the present invention provides a method for preparing any composition described herein.

In some embodiments, the enhancing muscle function includes: alleviating or inhibiting muscular dysfunction, optimizing mitochondrial function in muscle, ameliorating insulin resistance in muscle, increasing muscle mass or muscular strength, mitigating or preventing muscle loss, boosting exercise performance, increasing number of skeletal muscle fibers and making adjacent muscle fibers align tightly, In some embodiments, the enhancing muscle function is by increasing ATP production, scavenging chronic ROS, or activating the AMPK/SIRT1/PGC-1α mitochondrial biogenesis signaling pathway.

These and other features, aspects, and advantages of the present invention will become better understood with reference to the following description and appended claims.

DETAILED DESCRIPTION OF THE INVENTION

In the Summary Section above and the Detailed Description Section, and the claims below, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

As used herein, the term "or" is meant to include both "and" and "or." In other words, the term "or" may also be replaced with "and/or."

As used herein, the singular forms "a," "an" and "the" are intended to include the plural forms as well, unless the context clearly indicates otherwise.

As used herein, the term "comprise" or "include" and their conjugations, refer to a situation where said terms are used in their non-limiting sense to mean that items following the word are included, but items not specifically mentioned are not excluded. It also encompasses the more limiting verb "to consist essentially of" and "to consist of".

The present invention provides novel methods or compositions for enhancing muscle function in a mammal.

In a first aspect, the present invention provides methods for enhancing muscle function in a mammal, the method includes administration to the mammal of a composition including therapeutically effective amount of dihydroberberine (DHB) or a pharmaceutically acceptable salt, acid, ester, analog or derivative thereof.

As mentioned above, unhealthy lifestyles and diets have resulted in muscular dysfunction for many people nowadays. Once the muscular dysfunction occurs, it will have severe health consequences, such as impaired locomotory function, compromised balance, inadequate carbohydrate metabolism (like obesity and diabetes), increased risk of fall and fractures, all of which diminish the quality of life in the daily life.

Berberine (BBR), a traditional Chinese medicine, is a natural plant alkaloid originally isolated from extracts of *Berberis aristata* and *Coptis chinensis* (Huanglian). In recent years, multiple effects of BBR have been demonstrated to mimic a low-carbohydrate diet and promote insulin sensitivity (See, e.g., Yu, Y., et al., *Berberine Improves Cognitive Deficiency and Muscular Dysfunction via Activation of the AMPK/SIRT1/PGC-1α Pathway in Skeletal Muscle from Naturally Aging Rats*. J Nutr Health Aging, 2018. 22(6): p. 710-717). The inventors of this application have surpringly found that dihydroberberine (DHB), a hydrogenated derivative of BBR, provide similar but even better benefits than BBR. Such benefits include but are not limited to improving the insulin resistance in the whole body and skeletal muscle, enhancing the activity of glucose transporters, increasing the number of skeletal muscle fibers, making adjacent muscle fibers align tightly, promote ATP production, scavenging chronic reactive oxygen species (ROS) and activating the AMPK/SIRT1/PGC-1α mitochondrial biogenesis signaling pathway in the muscle tissue.

As used herein, the term "administration" refers to the process of delivering a disclosed combination, composition or kit to a subject. The combination, compositions or kits can be administered in a variety of ways, including orally, intragastrically, and parenterally (e.g., intravenous and intraarterial as well as other suitable parenteral routes), and the like.

As used herein, the term "pharmaceutically acceptable" means pharmaceutically, physiologically, alimentarily, or nutritionally acceptable, and refers to those compositions or combinations of agents, materials, or compositions, and/or their dosage forms, which are within the scope of sound medical judgment, suitable for use in contact with the tissues of human beings and animals without excessive toxicity, irritation, allergic response, or other problem or complication, commensurate with a reasonable benefit/risk ratio.

As used herein, the term "effective amount" refers to an amount that is required to achieve the effect as taught herein. It will be understood, however, that the total daily usage of dihydroberberine (DHB) or its analog or its derivatives may be decided by the attending physician within the scope of sound medical judgment. The specific therapeutically effective dose level for any particular subject will depend upon a variety of factors including the disorder being treated and the severity of the disorder; the specific composition employed, the age, body weight, general health, sex and diet of the subject; the time of administration, route of administration, and rate of excretion of dihydroberberine (DHB) or its analog or its derivatives employed; the duration of the treatment; drugs used in combination or coincidental with dihydroberberine (DHB) or its analog or its derivatives; and like factors well known in the medical arts. For example, it is well known within the skill of the art to start doses of the compound at levels lower than those required to achieve the desired therapeutic effect and to gradually increase the dosage until the desired effect is achieved.

One of skill in the art recognizes that an amount may be considered therapeutically "effective" even if the condition is not totally eradicated or prevented, but it or its symptoms and/or effects are improved or alleviated partially in the subject.

In some embodiments, the composition includes from about 5% to about 10%, 20%, 30%, 40%, 50%, 60%, 70%, 80%, 90%, or 95% by weight of dihydroberberine (DHB) or its analog or its derivatives, and preferably from about 30% to about 90%/c by weight of dihydroberberine (DHB) or its analog or its derivatives, based upon the total weight of the composition taken as 100% by weight.

In some embodiments, the enhancing muscle function includes: alleviating or inhibiting muscular dysfunction, optimizing mitochondrial function in muscle, ameliorating insulin resistance in muscle, increasing muscle mass or muscular strength, mitigating or preventing muscle loss, and boosting exercise performance.

In some embodiments, the enhancing muscle function is increasing muscle mass.

In some embodiments, the enhancing muscle function is improving insulin resistance in skeletal muscle.

In some embodiments, the enhancing muscle function is changing morphology of skeletal muscle, such as increasing number of skeletal muscle fibers and making adjacent muscle fibers align tightly.

In some embodiments, the enhancing muscle function is by increasing ATP production, scavenging chronic ROS, or activating AMPK/SIRT1/PGC-1α mitochondrial biogenesis signaling pathway in muscle tissue.

As used herein, the term "mammal" or "subject" may be used interchangeably to refer to any animal to which the presently disclosed methods and compositions may be applied or administered. The animal may have an illness or other disease, but the animal does not need to be sick to benefit from the presently disclosed methods and compositions. "Mammal" includes, without limitation, mice, rats, rabbits, guinea pigs, dogs, cats, sheep, goats, cows, horses, primates, such as monkeys, chimpanzees, and apes, and, in particular, humans.

As used herein, "pet" includes, without limitation, mice, rats, rabbits, guinea pigs, dogs, cats, and sheep.

In some embodiments, the mammal is human, a cattle, or a pet.

In some embodiments, the composition is prepared in a form of drink, nutritional supplement, cosmetic product, or pharmaceutical composition.

In some embodiments, DHB or its analog or its derivatives are administered at a daily dose of 10 mg-2000 mg.

The dosage may range broadly, depending upon the desired effects and the therapeutic indication. The daily dosage regimen for an adult human patient may be, for example, an oral dose of between 0.01 mg and 3000 mg of dihydroberberine or its metabolites, preferably between 1 mg and 700 mg, e.g., 5 to 200 mg, or between about 0.1 mg and about 1,000 mg of dihydroberberine or its metabolites per kg of body weight of the subject. The dosage may be a single one or a series of two or more given in the course of one or more days, as is needed by the subject. In some embodiments, the compounds are administered for a period of continuous therapy, for example for a week or more, or for months or years. In some embodiments, dihydroberberine or its metabolites, or a pharmaceutically acceptable salt thereof, can be administered less frequently compared to the frequency of administration of an agent within the standard of care. In some embodiments, dihydroberberine or its metabolites, or a pharmaceutically acceptable salt thereof, can be administered one time per day. In some embodiments, the total time of the treatment regime with dihydroberberine or its metabolites, or a pharmaceutically acceptable salt thereof, can be less compared to the total time of the treatment regime with the standard of care.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). the dose and perhaps dose frequency, will also vary according to the age, body weight, and response of the individual patient. A program comparable to that discussed above may be used in veterinary medicine.

In some embodiments, the daily dose is administered in divided doses or a single dose.

In some embodiments, the administration is at least once a day or more times a day.

In some embodiments, the administration is at least 7 days and above in one period.

Multiple techniques of administering a composition exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. One may also administer the composition in a local rather than systemic manner, for example, via injection of the compound directly into the infected area, often in a depot or sustained release formulation. Furthermore, one may administer the composition in a targeted drug delivery system, for example, in a liposome coated with a tissue specific antibody. The liposomes will be targeted to and taken up selectively by the organ.

In some embodiments, the administration is through various routes selected from oral, intravenous injectable, intramuscular injectable, intraperitoneal, topical, or sublingual route.

"Intraperitoneal" as used here means within or administered through the peritoneum. The peritoneum is a thin, transparent membrane that lines the walls of the abdominal (peritoneal) cavity and contains/encloses the abdominal organs such as the stomach and intestines.

As used herein, "sublingual" refers to situated or applied under the tongue.

In some embodiments, dihydroberberine (DHB) or its analog or its derivatives are salts, polymers, esters, or acid.

In some embodiments, dihydroberberine (DHB) or its analog or its derivatives are formulated in solutions, liquid suspensions, parenteral solutions, injections, microemulsion, tablets, pills, granules, powder, film, (micro)capsules, aerosols, tonics, or syrups, beverages, nutritional supplements, snacks, bars, gums, sugars, sublingual articles, or functionalized foods.

"Sublingual articles" include articles that are dissolved under the tongue.

"Functionalized foods" include foods that have a potentially positive effect on health beyond basic nutrition.

In a second aspect, the present invention provides a composition including therapeutically effective amount of dihydroberberine (DHB) or a pharmaceutically acceptable salt, acid, ester, analog or derivative thereof, for enhancing muscle function.

In some embodiments, the enhancing muscle function includes, but not limited to, alleviating or inhibiting muscular dysfunction, optimizing mitochondrial function in muscle, ameliorating insulin resistance in muscle, increasing muscle mass and muscular strength, mitigating or preventing muscle loss, boosting exercise performance, increasing number of skeletal muscle fibers and making adjacent muscle fibers align tightly, In some embodiments, the enhancing muscle function is by increasing ATP production, scavenging chronic ROS, or activating the AMPK/SIRT1/PGC-1α mitochondrial biogenesis signaling pathway.

In a third aspect, the present invention provides use of any composition described herein, for enhancing muscle function.

In a fourth aspect, the present invention provides a method for preparing any composition described herein.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead are merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a composition, composition or device, the term "comprising" means that the composition, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

Any titles or subheadings used herein are for organization purposes and should not be used to limit the scope of embodiments disclosed herein.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

Example 1

Experimental Protocols.

Male Sprague Dawley rats aged 6-8 weeks were housed under a 12/12 h light/dark cycle at 22° C. and given free access to water and high-fat diet (HFD, 60% kcal from fat) for 12 weeks. After the 12 weeks, all rats were randomly divided into 3 groups of 8 animals. They were supplemented with or without DHB according to the following:
(1) non-supplement group (Con HFD only, Group 1);
(2) DHB supplement group (DHB+HFD, 100 mg/kg, Group 2);
(3) DHB supplement group (DHB+HFD, 200 mg/kg, Group 3).

Before supplementing DHB, the muscle content of all rats was measured by nuclear magnetic resonance body composition analyzer. And then all rats were administered DHB before each major meal once daily by gavage (i.g.) in normal saline solution for 4 months. The muscle content of all rats was tested by nuclear magnetic resonance body composition analyzer every month.

Before the rats were sacrificed, half the rats in each group were injected with 0.75 IU/kg body weight insulin (i.p.) to activate glucose uptake and assess the insulin resistance in the skeletal muscle. Fifteen minutes later, all the rats were anesthetized with chloral hydrate; the soleus muscles were fixed in paraformaldehyde, and the gastrocnemius muscles were frozen immediately in liquid nitrogen and stored at −80° C. for protein-related experiments.

Results:

1. DHB decreases body fat and increases muscle mass effectively.

Figure 1:
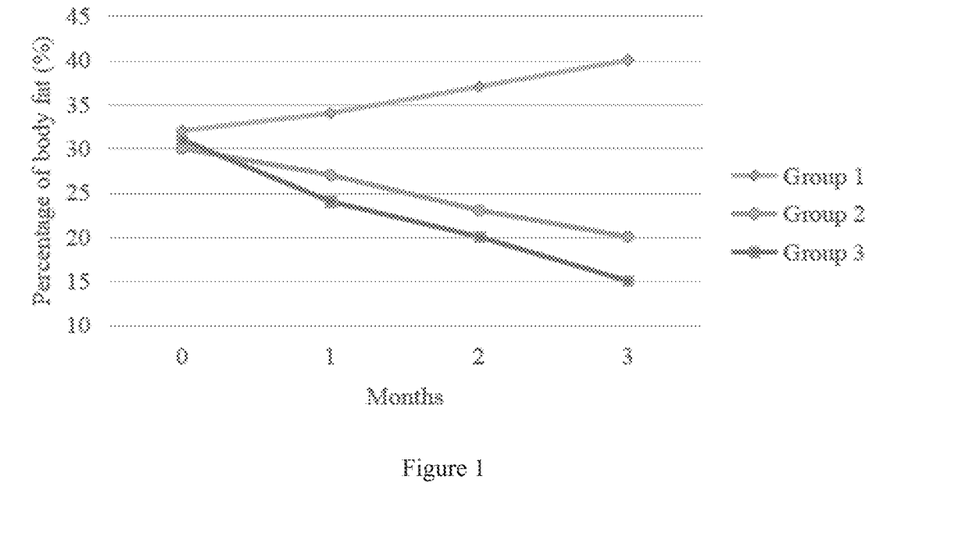
FIG. 1 is a graph of percentage of body fat of three groups of rats (Con; DHB 100 mg/kg; DHB 200 mg/kg) every month.

To prove that DHB can increase muscle mass, all percentage of body fat data tested by nuclear magnetic resonance body composition analyzer was compared. FIG. 1 is a graph of percentage of body fat of three groups of rats (Con; DHB 100 mg/kg; DHB 200 mg/kg) every month. As shown in FIG. 1, over the course of the study, administration of DHB had a greater reduction in body fat compared to control group (group 1), especially the percentage of body fat in the higher dose group decreased about 52% than at the beginning of supplementation, indicating that DHB administration could increase muscle mass significantly. Thus, DHB supplementation could achieve the beneficial effects on weight loss and increasing muscle mass.

2. DHB improves insulin resistance in the skeletal muscle.

Figure 2:
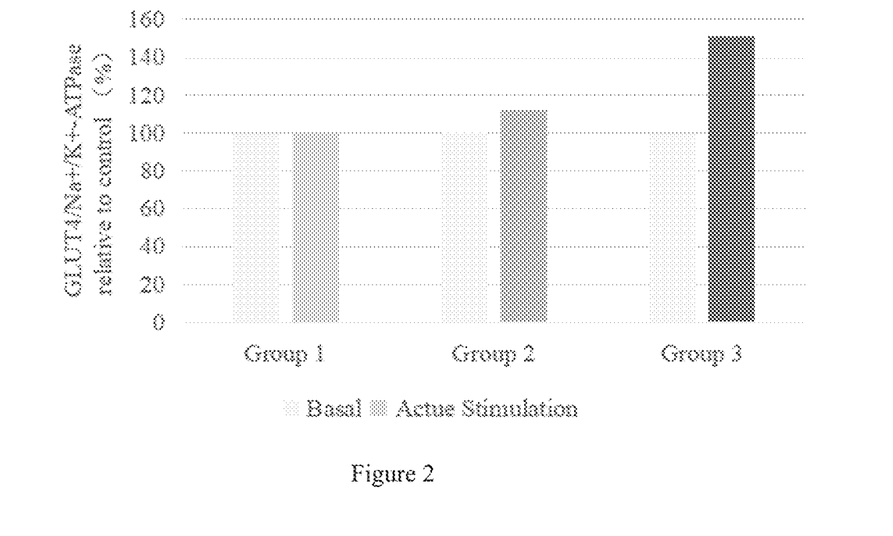
FIG. 2 is a graph of the relative expression of GLUT4 in skeletal muscle in three groups of rats (Con; DHB 100 mg/kg; DHB 200 mg/kg).

To assess that DHB could improve insulin resistance in the skeletal muscle, the insulin stimulating membrane translocation of glucose transporter type 4 (GLUT4) by the western blot analysis was measured and compared among the groups. FIG. 2 is a graph of the relative expression of GLUT4 in skeletal muscle in three groups of rats (Con; DHB 100 mg/kg; DHB 200 mg/kg). In FIG. 2, it was observed that the membrane translocation of GLUT4 was remarkably increased after insulin stimulation in DHB groups relatively to control group (group 1), especially in the higher dose group. Thus, DHB supplementation could achieve the beneficial effects on ameliorating insulin resistance in the skeletal muscle.

3. DHB changes the morphology of the skeletal muscle, such as increasing the number of skeletal muscle fibers and making adjacent muscle fibers align tightly.

To evaluate the morphological changes of the skeletal muscle, HE staining of soleus was conducted. Hematoxylin-eosin (HE) staining: Soleus muscles were fixed in paraformaldehyde overnight, dehydrated in an ascending graded ethanol series, equilibrated with xylene, embedded in paraffin and sectioned into 5- to 10-μm slices. Then, the samples were dewaxed with xylene and a descending graded ethanol series. Sections were stained with Mayer's hematoxylin and eosin. Observe the morphological changes by biological microscope.

Figure 3A:
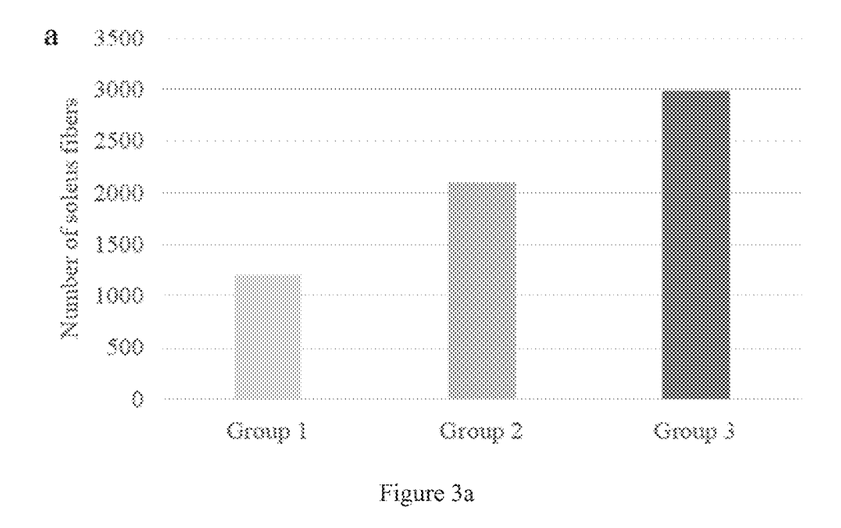
FIG. 3a is a graph of the number of soleus fibers in three groups of rats (Con; DHB 100 mg/kg; DHB 200 mg/kg).
Figure 3B:
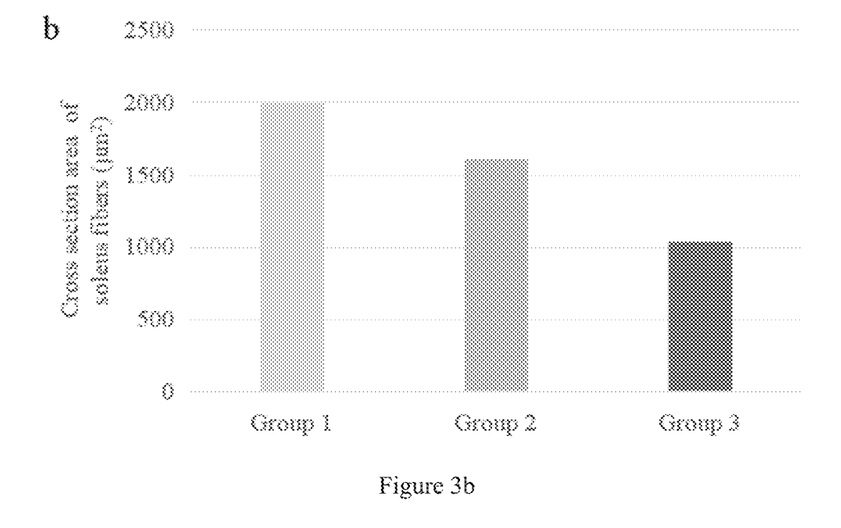
FIG. 3b is a graph of cross section area of soleus fiber in three groups of rats (Con; DHB 100 mg/kg; DHB 200 mg/kg).

FIG. 3a is a graph of the number of soleus fibers in three groups of rats (Con; DHB 100 mg/kg; DHB 200 mg/kg). FIG. 3b is a graph of cross section area of soleus fiber in three groups of rats (Con; DHB 100 mg/kg; DHB 200 mg/kg). In the DHB supplementation group, especially in group 3, the number of muscle fibers increased dramatically compared with the control group (FIG. 3a), and the relative cross-sectional area of the muscle fibers dropped below that of the control group (FIG. 3b)

4. DHB increases ATP production, scavenges chronic ROS, and protect and improve mitochondrial function in skeletal muscle by activating the AMPK/SIRT1/PGC-1α mitochondrial biogenesis signaling pathway in the muscle tissue.

Based on the results of decreased fiber number and insulin resistance, the mitochondrial function in skeletal muscle might be also impaired. ATP and ROS levels in serum and skeletal muscle, which represented mitochondrial function, were further determined.

AMPK/SIRT1/PGC-1α are the key regulators of mitochondrial biogenesis, and DHB has been proven to be the activator of AMPK in various filed. Therefore, the protective mechanism of DHB on mitochondrial function of skeletal muscle may be via the AMPK/SIRT1/PGC-1α-dependent mitochondrial biogenesis pathway.

Protein sample preparation: For total protein extraction, 100 mg of the frozen gastrocnemius muscle was homogenized in radioimmunoprecipitation assay (RIPA) buffer (containing 0.2 μg/mL PMSF and 10 μg/mL phosphatase inhibitor) for 30 min and then centrifuged at 3,500 rpm×15 min and 12,000 rpm×15 min. The supernatants were extracted for the western blot analysis.

For plasma membrane protein isolation, 100 mg of frozen gastrocnemius muscle from each sample was used. Plasma membrane proteins were isolated according to the kit manufacturer's instructions, and the end product was dissolved in 100 μl of PBS containing 5% SDS.

Western blot analysis: The concentration of protein in the gastrocnemius muscle was quantitated by piercing bicinchoninic acid (BCA), and 120 μg of total protein was electrophoresed on a 12% SDS polyacrylamide gel and electro-transferred onto Polyvinylidene difluoride (PVDF) membranes. Membranes were blocked with 5% (w/v) BSA for 2 h at room temperature and then incubated with primary antibodies overnight at 4° C. with slight shaking. After being washed with TBST three times, the membranes were incubated with a secondary antibody (1:2000) at room temperature for 2 h. The protein bands were visualized by enhanced chemiluminescence with a GENE Imaging system. The images were quantified using Image Analysis Software.

Reactive oxygen species (ROS) test: Ten microliters of skeletal muscle or lysate or 10 μl of serum was added to 127.5 μl of reaction buffer in 96-well plates (containing 30 mM HEPES (pH 7.2), 200 mM KCl, 1 mM $MgCl_2$, and 7.5 μl of 2,2'-azobis(2-methylpropionamidine) dihydrochloride). The same volume of ultrapure water was pipetted into the plate as a blank. The microplate was put into a fluorescence microplate reader at 35° C. 10 μl of the fluorescent probe H2DCF-DA was added to each well for a final concentration of 40 μM immediately before reading, and the level of ROS was detected at 488 and 525 nm.

ATP determination: The ATP concentration in the gastrocnemius muscle was measured using ELISA according to the manufacturer's instructions. Before the ELISA was tested, the gastrocnemius muscle lysates were first measured with a BCA protein assay kit, and the total protein concentration of each group was adjusted to the same by RIPA. The concentration of ATP was then calculated based on the absorption density determined at 450 nm.

Western blot was used to check the protein expression of AMPK/SIRT1/PGC-1α in the muscle tissue.

Figure 4A:
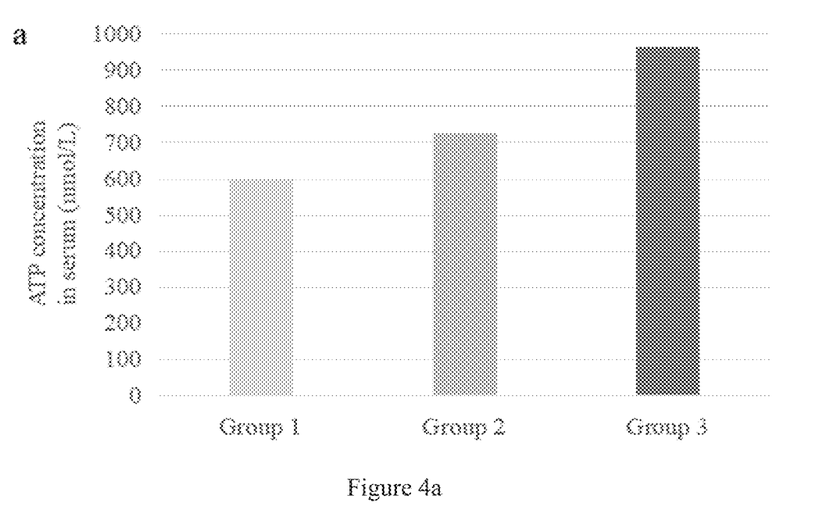
FIGS. 4a and 4b are graphs of the levels of ATP and ROS in serum in three groups of rats (Con; DHB 100 mg/kg; DHB 200 mg/kg).
Figure 4B:
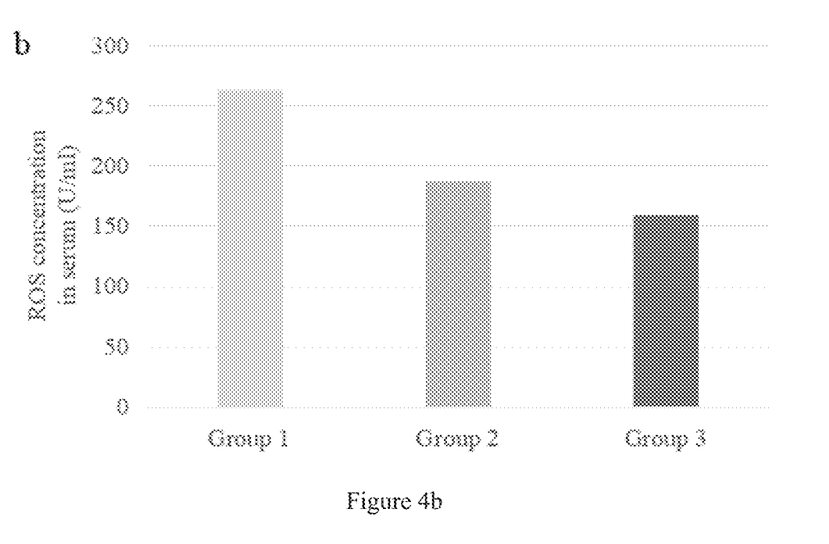
Figure 4C:
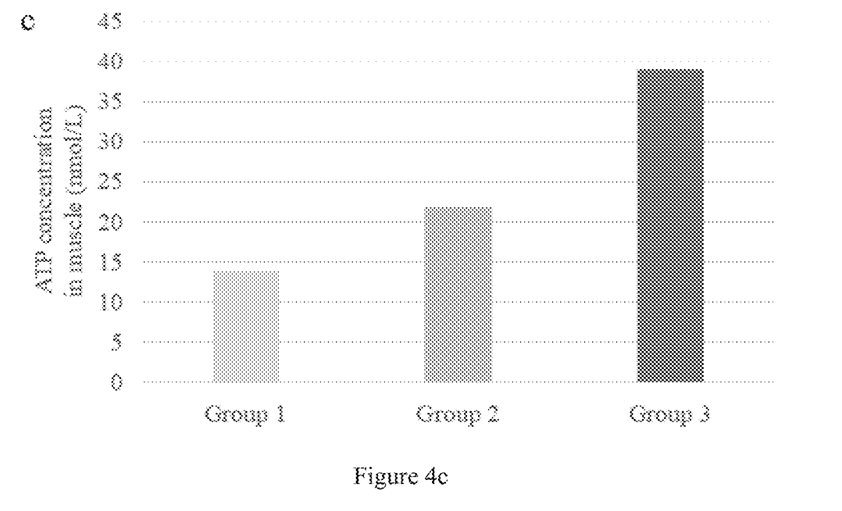
FIGS. 4c and 4d are graphs of the levels of ATP and ROS in skeletal muscle in three groups of rats (Con; DHB 100 mg/kg; DHB 200 mg/kg).
Figure 4D:
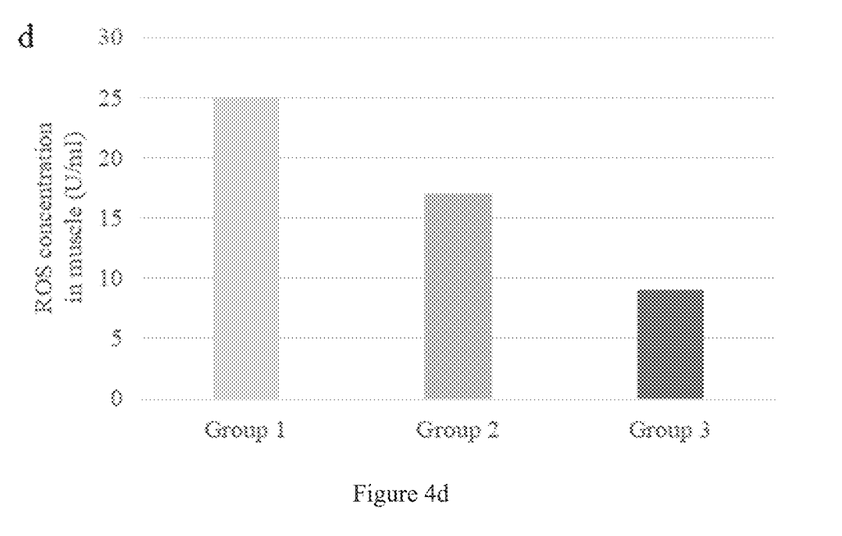
Figure 4E:
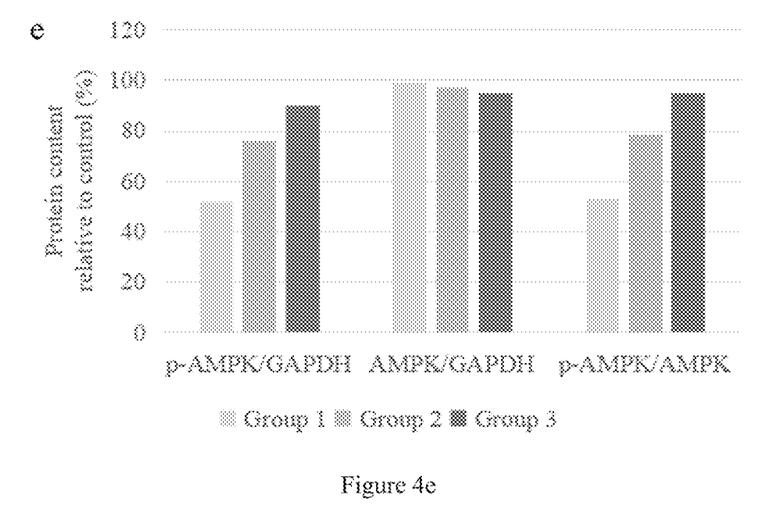
FIG. 4e-4g are graphs of the relative expression levels of p-AMPK/SIRT1/PGC-1α protein in skeletal muscle in three groups of rats (Con; DHB 100 mg/kg; DHB 200 mg/kg).
Figure 4F:
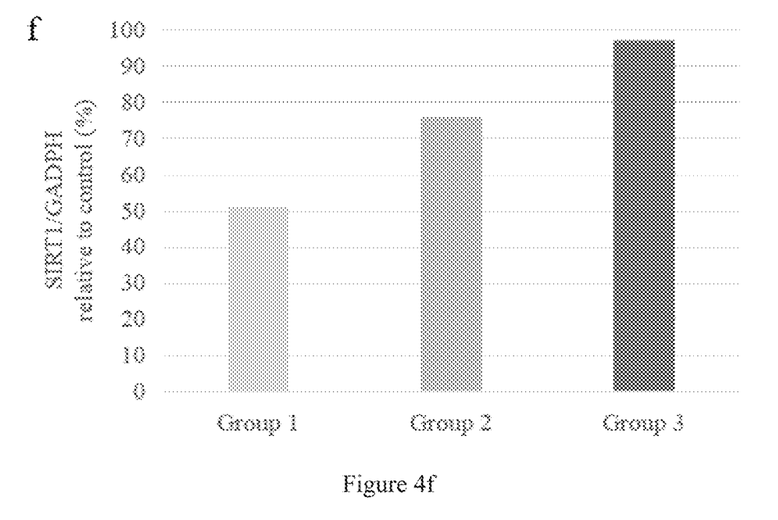
Figure 4G:
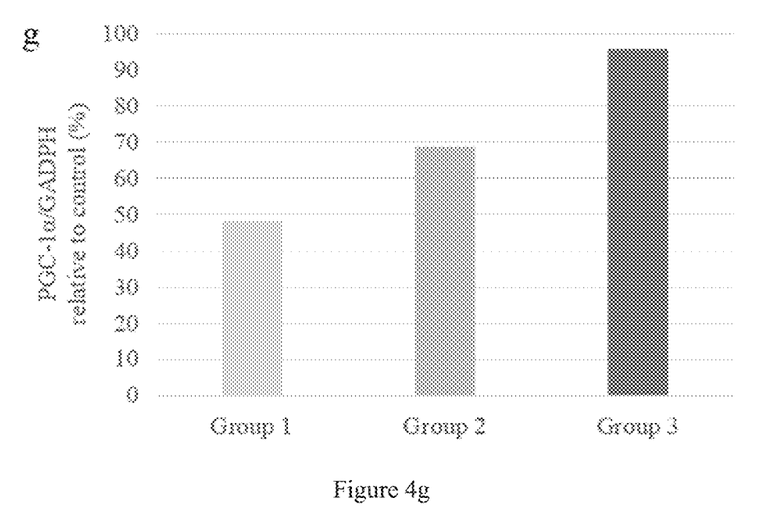

FIGS. 4a and 4b are graphs of the levels of ATP and ROS in serum in three groups of rats (Con; DHB 100 mg/kg; DHB 200 mg/kg). FIGS. 4c and 4d are graphs of the levels of ATP and ROS in skeletal muscle in three groups of rats (Con; DHB 100 mg/kg; DHB 200 mg/kg). FIG. 4e-4g are graphs of the relative expression levels of p-AMPK/SIRT1/PGC-1α protein in skeletal muscle in three groups of rats (Con; DHB 100 mg/kg; DHB 200 mg/kg). From FIGS. 4a and 4c, with DHB treatment, the production of ATP was increased significantly, especially in the higher dose of DHB group (200 mg/kg), the production of ATP in serum and skeletal muscle are 1.6- and 2.7-fold than that in the control group (group 1). Moreover, in FIGS. 4b and 4d, administration of DHB could inhibit increased ROS effectively in serum and skeletal muscle. In FIG. 4e, using GAPDH as an internal reference, there is no significant difference in total AMPK protein expression among the three groups. However, the protein expression of p-AMPK was dramatically upregulated in DHB groups, especially in group 3. Furthermore, SIRT1 and PGC-1α presented the same protein expression trend as p-AMPK. In group 3, the protein expression of SIRT1 and PGC-la increased remarkably by approximately 1.9- and 2-fold relative to the control group (FIG. 4f-4g). These data suggest that DHB administration scavenged chronic ROS and increased ATP production in both serum and skeletal muscle. In addition, DHB could protect and improve mitochondrial function in skeletal muscle via activating AMPK/SIRT1/PGC-1α-dependent mitochondrial biogenesis pathway.

What is claimed is:

1. A method for enhancing muscle function in a mammal, the method comprising:
   administrating to the mammal in need thereof of a composition comprising an effective amount of dihydroberberine (DHB) or a pharmaceutically acceptable salt, acid, or ester thereof.

2. The method of claim 1, wherein the enhancing muscle function comprises:
   alleviating or inhibiting muscular dysfunction, improving mitochondrial function in muscle, ameliorating insulin resistance in muscle, increasing muscle mass or muscular strength, mitigating or preventing muscle loss, and boosting exercise performance.

3. The method of claim 1, wherein the enhancing muscle function is improving insulin resistance in skeletal muscle, or changing morphology of skeletal muscle.

4. The method of claim 1, wherein the enhancing muscle function is by scavenging chronic ROS, or activating AlVIPK/SIRT1/PGC-1α mitochondrial biogenesis signaling pathway in muscle tissue.

5. The method of claim 1, wherein the mammal is a human or a cattle or a pet.

6. The method of claim 1, wherein the composition is prepared in a form of nutritional or drinking or pabulary or pharmaceutical composition as such and used in food, drink, nutritional, cosmetic, or pharmaceutical field.

7. The method of claim 1, wherein the dihydroberberine or its analog or its derivatives is administered at a daily dose of 10 mg-2000 mg.

8. The method of claim 1, wherein the administration is through various routes selected from oral, intravenous injectable, intramuscular injectable, intraperitoneal, topical, or sublingual route.

9. The method of claim 1, wherein the dihydroberberine or its analog or its derivatives is formulated in solutions, liquid suspensions, parenteral solutions, injections, microemulsion, tablets, pills, granules, powders, film, (micro) capsules, aerosols, tonics, or syrups, beverages, nourishments, snacks, gums, bars, sugars, sublingual articles, or functionalized foods.

10. The method of claim 1, wherein the enhancing muscle function is by increasing ATP production.

* * * * *